US012125199B2

(12) United States Patent
Oh et al.

(10) Patent No.: US 12,125,199 B2
(45) Date of Patent: Oct. 22, 2024

(54) METHOD FOR PREDICTING DISEASE BASED ON MEDICAL IMAGE

(71) Applicant: VUNO Inc., Seoul (KR)

(72) Inventors: Hyunwoo Oh, Seoul (KR); Sejin Park, Yongin-si (KR); Jinkyeong Sung, Seoul (KR); Weon Jin Kim, Seoul (KR); Eunpyeong Hong, Seongnam-si (KR); Dong Soo Lee, Seoul (KR)

(73) Assignee: VUNO Inc., Seoul (KR)

( * ) Notice: Subject to any disclaimer, the term of this patent is extended or adjusted under 35 U.S.C. 154(b) by 391 days.

(21) Appl. No.: 17/539,827

(22) Filed: Dec. 1, 2021

(65) Prior Publication Data

US 2022/0180512 A1    Jun. 9, 2022

(30) Foreign Application Priority Data

Dec. 4, 2020    (KR) .................... 10-2020-0168183

(51) Int. Cl.
  *G06T 7/00*    (2017.01)
  *A61B 5/00*    (2006.01)
  (Continued)

(52) U.S. Cl.
  CPC .......... *G06T 7/0012* (2013.01); *A61B 5/0042* (2013.01); *A61B 5/7264* (2013.01); *A61B 5/7275* (2013.01); *G06N 3/045* (2023.01); *G06T 7/11* (2017.01); *G06T 7/30* (2017.01); *G16H 30/40* (2018.01); *G16H 50/20* (2018.01); *A61B 5/055* (2013.01); *A61B 5/4088* (2013.01); *G06T 2207/20084* (2013.01); *G06T 2207/30016* (2013.01)

(58) Field of Classification Search
  None
  See application file for complete search history.

(56) References Cited

U.S. PATENT DOCUMENTS 10,898,152 B1    1/2021  Kim et al.
2015/0269315 A1   9/2015  Arakita et al.
(Continued)

FOREIGN PATENT DOCUMENTS

JP           6415812 B2      10/2018
KR        10-1943011 B1       1/2019
(Continued)

OTHER PUBLICATIONS

Fulton, "Machine Learning Approaches for Identification of Alzheimer's Disease using Social Determinants & Imagery," poster presented at the Texas State University Health Scholar Showcase, San Marcos, Texas, Feb. 23, 2018.

*Primary Examiner* — Leon Flores
(74) *Attorney, Agent, or Firm* — Seed IP Law Group LLP

(57) ABSTRACT

Disclosed is a method for predicting disease based on a medical image performed by a computing device. The method includes: generating a feature vector related to predictive values of brain disease for each of 2D medical images included in a 3D medical image, using a pre-trained first model; estimating importance indicating prediction accuracy for each of the 2D medical images based on the feature vector, using a pre-trained second model; and selecting at least one model input image suitable for prediction of the brain disease from among the 2D medical images based on the importance.

14 Claims, 12 Drawing Sheets

(51) Int. Cl.
*G06N 3/045* (2023.01)
*G06T 7/11* (2017.01)
*G06T 7/30* (2017.01)
*G16H 30/40* (2018.01)
*G16H 50/20* (2018.01)
A61B 5/055 (2006.01)

(56) References Cited

U.S. PATENT DOCUMENTS

2020/0027557 A1 1/2020 Karow et al.
2020/0098108 A1* 3/2020 Huo .................. G06T 7/0014

FOREIGN PATENT DOCUMENTS

| | | |
|---|---|---|
| KR | 10-1995383 B1 | 7/2019 |
| KR | 10-2019-0112219 A | 10/2019 |
| KR | 10-2165840 B1 | 10/2020 |
| KR | 10-2179587 B1 | 11/2020 |
| TW | 202042250 A | 11/2020 |

\* cited by examiner

METHOD FOR PREDICTING DISEASE BASED ON MEDICAL IMAGE

CROSS-REFERENCE TO RELATED APPLICATIONS

This application claims priority to and the benefit of Korean Patent Application No. 10-2020-0168183 filed in the Korean Intellectual Property Office on Dec. 4, 2020, the entire contents of which are incorporated herein by reference.

BACKGROUND

Technical Field

The present disclosure relates to a method of processing a medical image, and more particularly, to a method of selecting a medical image and predicting disease based on information about a medical image effective for determining disease by using a neural network.

Description of the Related Art

Medical images are data that enables people to understand physical states of various organs in the human body. The medical image includes a digital radiographic image (X-ray), a Computed Tomography (CT) image, a Magnetic Resonance Imaging (MRI) image, or the like.

There are medical image processing technologies that determine the presence of a specific disease based on a three-dimensional (3D) medical image obtained by photographing body organs. Most of the related arts predict a specific disease by using a 3D medical image as an input to a 3D neural network model as it is. For example, one of the related arts determines Alzheimer's dementia based on a 3D magnetic resonance image obtained by photographing the brain structure by using a 3D convolutional neural network.

Korean Patent Application Laid-Open No. 10-2019-0112219 (Oct. 4, 2019) discloses a method of detecting Alzheimer's disease.

BRIEF SUMMARY

The inventors of the present disclosure have recognized one or more technical problems in the related art in that it takes a considerable amount of time for a calculation for predicting a specific disease due to the amount of information of the 3D medical image, complexity of the 3D neural network model itself, and the like. That is, some approaches in the related art using the 3D medical image consume a considerable amount of computing resources for the calculation for predicting a specific disease and has a quite slow operation speed, so that real-time analysis is virtually impossible. In order to solve the problem, it may be considered to apply newly proposed technologies in relation to a 2D neural network model. However, the inventors of the present disclosure appreciated that due to the difference in the speed of technological development between 3D image analysis and 2D image analysis, there is also a problem in that it is difficult to simply apply techniques newly proposed for 2D image analysis to 3D image analysis.

In order to solve the problem in the related art, it may be considered to use a 2D medical image generated through processing a 3D medical image for predicting a specific disease. However, when all of the 2D medical images generated from the 3D medical image are used for predicting a specific disease, significant computational cost is inevitably required like the related arts. Accordingly, it may be considered that it is beneficial to properly select and use a 2D medical image necessary for predicting a specific disease in the analysis of the medical image.

The present disclosure has been conceived in response to one or more technical problems in the related art including the above identified problems identified by the inventors of the present disclosure. The present disclosure provides a method of selecting a medical image and predicting disease based on information about a medical image optimized to determine disease.

In order to solve the foregoing object, a first embodiment of the present disclosure discloses a method for predicting disease based on a medical image performed by a computing device, the method including: generating a feature vector related to predictive values of brain disease for each of 2D medical images included in a 3D medical image, using a pre-trained first model; estimating importance indicating prediction accuracy for each of the 2D medical images based on the feature vector, using a pre-trained second model; and selecting at least one model input image suitable for prediction of the brain disease from among the 2D medical images based on the importance.

In an alternative embodiment, the method may further include extracting a brain parenchyma region from each of the 2D medical images in which a position of a brain region is aligned with respect to a template, using a pre-trained third model.

In the alternative embodiment, the first model may generate the feature vector based on the 2D medical images, personal information about a subject of the 3D medical image, and number information indicating positions of the 2D medical images in the 3D medical image.

In the alternative embodiment, the neural network model may perform pre-processing of removing an image in which a true label has a predetermined number of pixels or less among the input images in a training process.

In the alternative embodiment, the first model may include a first neural network extracting features for prediction of the brain disease from the 2D medical images; and a second neural network that outputs the predictive values of brain disease for each of the 2D medical images, based on the features extracted by the first neural network, the personal information, and the number information.

In the alternative embodiment, the importance may be estimated based on a tree boosting algorithm used in the second model which takes the feature vector as input.

In the alternative embodiment, the selecting the at least one model input image suitable for prediction of the brain disease may include: selecting at least one of the 2D medical images as the model input image by comparing the importance and a threshold value; and obtaining reference number information indicating a position of the selected model input image in the 3D medical image.

In the alternative embodiment, the method may further include using the selected at least one model input image as training data for a disease diagnosis model.

In order to solve the foregoing object, a second embodiment of the present disclosure discloses a method for predicting disease based on a medical image, performed by a computing device. The method includes: generating information for parcellating at least one brain region present in each of 2D medical images included in a 3D medical image, using a pre-trained segmentation model; and selecting at least one model input image suitable for prediction of a brain disease from among the 2D medical images based on the generated information for parcellating.

In an alternative embodiment, an image satisfying a predetermined condition related to a reference region among the 2D medical images may be selected as the at least one model input image suitable for prediction of the brain disease.

In an alternative embodiment, the reference region may include a medial temporal lobe, and the parcellated at least on brain region may include at least one of a hippocampus, a amygdala, a entorhinal cortex, a parahippocampal cortex, or a ventricle.

In the alternative embodiment, the method may further include using the selected at least one model input image as training data for a disease diagnosis model.

In order to solve the foregoing object, a third embodiment of the present disclosure discloses a method for predicting disease based on a medical image, performed by a computing device. The method includes: extracting a brain parenchyma region respectively from 2D medical images in which a position of a brain region is aligned based on a template, using a pre-trained preprocess model; selecting at least one model input image suitable for prediction of a brain disease from among the 2D medical images from which the brain parenchyma region is extracted; and predicting a presence probability of the brain disease based on the selected model input image, using a pre-trained disease diagnosis model.

In an alternative embodiment, the selecting the at least one model input image suitable for prediction of the brain disease may include selecting at least one image corresponding to reference number information among the 2D medical images from which the brain parenchyma region is extracted as the model input image, and the reference number information may be predetermined based on importance indicating prediction accuracy of the brain disease for each of the 2D medical images included in a 3D medical image.

In the alternative embodiment, the selecting the at least one model input image suitable for prediction of the brain disease may include: parcellating at least one brain region included in each of the 2D medical images from which the brain parenchyma region is extracted, using a pre-trained segmentation model; and selecting at least one model input image suitable for prediction of the brain disease from among the 2D medical images from which the brain parenchyma region is extracted based on information for the parcellated at least one brain region.

In the alternative embodiment, the disease diagnosis model may be trained based on at least one image selected as suitable for prediction of the brain disease among the 2D medical images included in a 3D medical image.

In order to solve the foregoing object, a first embodiment of the present disclosure discloses a computer program stored in a computer readable storage medium. When the computer program is executed in one or more processors, the computer program performs following operations for predicting disease based on a medical image, and the operations include: an operation of generating a feature vector including predictive values of brain disease for each of 2D medical images included in a 3D medical image, using a pre-trained first model; an operation of estimating importance indicating prediction accuracy for each of the 2D medical images based on the feature vector, using a pre-trained second model; and an operation of selecting at least one model input image suitable for prediction of the brain disease from among the 2D medical images based on the importance.

In order to solve the foregoing object, a second embodiment of the present disclosure discloses a computer program stored in a computer readable storage medium. When the computer program is executed in one or more processors, the computer program performs following operations for predicting disease based on a medical image, and the operations include: an operation of parcellating at least one brain region present in each of 2D medical images included in a 3D medical image, using a pre-trained segmentation model; and an operation of selecting at least one model input image suitable for prediction of a brain disease from among the 2D medical images based on information for the parcellated at least one brain region.

In order to solve the foregoing object, a first embodiment of the present disclosure discloses a computing device for predicting disease based on a medical image. The computing device includes: a processor including at least one core; a memory including program codes executable in the processor; and a network unit for receiving a medical image, and the processor generates a feature vector including predictive values of brain disease for each of 2D medical images included in a 3D medical image, using a pre-trained first model, estimates importance indicating prediction accuracy for each of the 2D medical images based on the feature vector, using a pre-trained second model, and selects at least one model input image suitable for prediction of the brain disease from among the 2D medical images based on the importance.

In order to solve the foregoing object, a second embodiment of the present disclosure discloses a computing device for predicting disease based on a medical image. The computing device includes: a processor including at least one core; a memory including program codes executable in the processor; and a network unit for receiving a medical image, and the processor parcellates at least one brain region present in each of 2D medical images included in a 3D medical image, using a pre-trained segmentation model; and selects at least one model input image suitable for prediction of a brain disease from among the 2D medical images based on information for the parcellated at least one brain region.

The present disclosure may provide a method of selecting a medical image and predicting disease based on information about a medical image optimized to determine disease.

DETAILED DESCRIPTION

Figure 1:
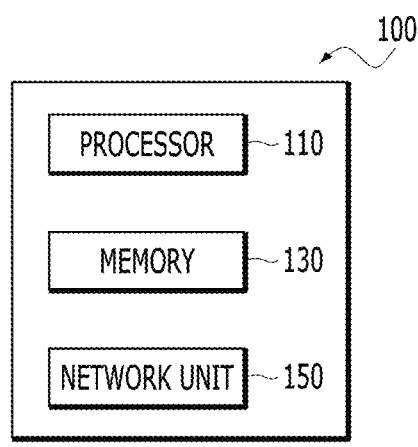
FIG. 1 is a block diagram of a computing device for predicting disease based on a medical image according to an embodiment of the present disclosure.

Various embodiments are described with reference to the drawings. In the present specification, various descriptions are presented for understanding the present disclosure. However, it is obvious that the embodiments may be carried out even without a particular description.

Terms, "component," "module," "system," and the like used in the present specification indicate a computer-related entity, hardware, firmware, software, a combination of software and hardware, or execution of software. For example, a component may be a procedure executed in a processor, a processor, an object, an execution thread, a program, and/or a computer, but is not limited thereto. For example, both an application executed in a computing device and a computing device may be components. One or more components may reside within a processor and/or an execution thread. One component may be localized within one computer. One component may be distributed between two or more computers. Further, the components may be executed by various computer readable media having various data structures stored therein. For example, components may communicate through local and/or remote processing according to a signal (for example, data transmitted to another system through a network, such as the Internet, through data and/or a signal from one component interacting with another component in a local system and a distributed system) having one or more data packets.

A term "or" intends to mean comprehensive "or" not exclusive "or." That is, unless otherwise specified or when it is unclear in context, "X uses A or B" intends to mean one of the natural comprehensive substitutions. That is, when X uses A, X uses B, or X uses both A and B, "X uses A or B" may be applied to any one among the cases. Further, a term "and/or" used in the present specification shall be understood to designate and include all of the possible combinations of one or more items among the listed relevant items.

It should be understood that a term "include" and/or "including" means that a corresponding characteristic and/or a constituent element exists. Further, a term "include" and/or "including" means that a corresponding characteristic and/or a constituent element exists, but it shall be understood that the existence or an addition of one or more other characteristics, constituent elements, and/or a group thereof is not excluded. Further, unless otherwise specified or when it is unclear in context that a single form is indicated in context, the singular shall be construed to generally mean "one or more" in the present specification and the claims.

The term "at least one of A and B" should be interpreted to mean "the case including only A," "the case including only B," and "the case where A and B are combined."

Those skilled in the art shall recognize that the various illustrative logical blocks, configurations, modules, circuits, means, logic, and algorithm operations described in relation to the embodiments additionally disclosed herein may be implemented by electronic hardware, computer software, or in a combination of electronic hardware and computer software. In order to clearly exemplify interchangeability of hardware and software, the various illustrative components, blocks, configurations, means, logic, modules, circuits, and operations have been generally described above in the functional aspects thereof. Whether the functionality is implemented as hardware or software depends on a specific application or design restraints given to the general system. Those skilled in the art may implement the functionality described by various methods for each of the specific applications. However, it shall not be construed that the determinations of the implementation deviate from the range of the contents of the present disclosure.

The description about the presented embodiments is provided so as for those skilled in the art to use or carry out the present disclosure. Various modifications of the embodiments will be apparent to those skilled in the art. General principles defined herein may be applied to other embodiments without departing from the scope of the present disclosure. Therefore, the present disclosure is not limited to the embodiments presented herein. The present disclosure shall be interpreted within the broadest meaning range consistent to the principles and new characteristics presented herein.

In the meantime, the term "image" or "mage data" used throughout the detailed description and the claims of the present disclosure refer to multidimensional data composed of discrete image elements (for example, pixels in a 2-dimensional image), and in other words, is the term referring to a target visible to the eye (for example, displayed on a video screen) or a digital representation of the target (for example, a file corresponding to a pixel output of a CT or MRI detector).

For example, "image" or "video" may be a medical image of a subject collected by Computed Tomography (CT), Magnetic Resonance Imaging (MRI), fundus image, ultrasonic rays, or other predetermined medical imaging systems publicly known in the art of the present disclosure. The image is not necessarily provided in a medical context, but may also be provided in a non-medical context, such as X-ray imaging for security screening.

Throughout the detailed description and the claims of the present disclosure, the "digital Imaging and Communications in Medicine (DICOM)" standard is a term collectively referring to various standards used in digital imaging expression and communication in medical devices, and the DICOM standard is published by the allied committee formed by the American College of Radiology (ACR) and American National Electrical Manufacturers Associations (NEMA).

Throughout the detailed description and the claims of the present disclosure, a "Picture Archiving and Communication System (PACS)" is a term that refers to a system that stores, processes, and transmits images in accordance with the DICOM standard, and medical images obtained by using digital medical imaging equipment, such as X-ray, CT, and MRI, may be stored in the DICOM format and transmitted to terminals inside and outside a hospital through a network, and a reading result and a medical record may be added to the medical image.

FIG. 1 is a block diagram of a computing device for predicting disease based on a medical image according to an embodiment of the present disclosure.

The configuration of a computing device 100 illustrated in FIG. 1 is merely a simplified example. In the embodiment of the present disclosure, the computing device 100 may include other configurations for performing a computing environment of the computing device 100, and only some of the disclosed configurations may also configure the computing device 100.

The computing device 100 may include a processor 110, a memory 130, and a network unit 150.

The processor 110 may be formed of one or more cores, and may include a processor, such as a central processing unit (CPU), a general purpose graphics processing unit (GPGPU), and a tensor processing unit (TPU) of the computing device, for performing a data analysis and deep learning. The processor 110 may read a computer program stored in the memory 130 and process data for machine learning according to an embodiment of the present disclosure. According to the embodiment of the present disclosure, the processor 110 may perform calculation for training a neural network. The processor 110 may perform a calculation, such as processing of input data for training in Deep Learning (DL), extraction of a feature from input data, an error calculation, and updating of a weight of the neural network by using back propagation, for training the neural network. At least one of the CPU, GPGPU, and TPU of the processor 110 may process training of a network function. For example, the CPU and the GPGPU may process training of the network function and data classification by using a network function together. Further, in the embodiment of the present disclosure, the training of the network function and the data classification by using a network function may be processed by using the processors of the plurality of computing devices together. Further, the computer program executed in the computing device according to the embodiment of the present disclosure may be a CPU, GPGPU, or TPU executable program.

According to the embodiment of the present disclosure, the processor 110 may receive a medical image including at least one brain region and select an image for effective for diagnosing a brain disease through a pre-trained machine learning model. The processor 110 may select at least one image required for predicting a brain disease among two-dimensional (2D) medical images included in a three-dimensional (3D) medical image by using at least one machine learning model. In this case, the process of selecting the image required for predicting the brain disease may be understood as a process of extracting information (for example, location information of the images selected within the 3D medical image) about the image effective for predicting the brain disease. The information about the image required for predicting the brain disease selected by the processor 110 may be stored in the memory 130. The processor 110 may pre-calculate information about an important image effective for determining the brain disease through the foregoing operation, and use the information for selecting an input image in the process of predicting the brain disease which is to be described below. Through this, the processor 110 may select and use the model input images optimized for prediction in accordance with the type of brain disease.

For example, the processor 110 may select at least one 2D slice image required for determining Alzheimer's dementia through a neural network model trained based on all of the 2D slice images included in a 3D magnetic resonance (MR) image and a machine learning model receiving output data of the neural network model. The processor 110 may acquire number information indicating where at least one 2D slice required for determining Alzheimer's dementia is located in the 3D MR image in the selection process. The processor 110 may select the acquired number information as a reference value for selecting the image for predicting Alzheimer's dementia. When a new 3D MR image is input for determining Alzheimer's dementia, the processor 110 may select a 2D slice image within a new 3D MR image based on the number information set as the reference value.

The processor 110 may train the neural network model for predicting the brain disease based on at least one image effective for diagnosing the brain disease selected through the foregoing operation. For example, the processor 110 may select at least one 2D slice image appropriate for determining Alzheimer's dementia among all of the 2D slice images included in the 3D MR image and establish a training data set. The processor 110 may train the neural network model for predicting Alzheimer's dementia based on the train data set consisting of at least one 2D slice images appropriate for determining Alzheimer's dementia. The foregoing training data set hardly contains noise data that interferes with the determination of Alzheimer's dementia. Accordingly, when the neural network model for predicting Alzheimer's dementia is trained based on the training data set, performance of dementia prediction may be significantly improved compared to the model in the related art trained based on all of the 2D slice images included in the 3D MR image.

According to an alternative embodiment of the present disclosure, the processor 110 may receive a medical image including at least one brain region and parcellate detailed regions of the brain existing in the input image by using a pre-trained neural network model. The processor 110 may select an image effective for diagnosing the brain disease based on information about the detailed regions of the brain parcellated through the neural network model. The processor 110 may parcellate the brain regions existing in the 2D medical images included in the 3D medical image by using the neural network model, and select at least one image required for predicting the brain disease based on the information about the parcellated brain regions. The processor 110 may determine, predict, or classify whether the brain disease exists based on the selected images according to the foregoing operation. Further, the processor 110 may train the neural network model for predicting the brain disease with the image effective for diagnosing the brain disease selected through the foregoing operation.

For example, the processor 110 may segment the brain region existing in the image received for diagnosing the brain disease into several detailed regions by using the neural network model trained based on at least one 2D slice image included in the 3D MR image. The processor 110 may select at least one 2D slice image required for determining Alzheimer's dementia from the received image according to a specific condition based on the information about the detailed regions of the brain. The processor 110 may determine whether Alzheimer's dementia exists based on at least one 2D slice image effective for predicting Alzheimer's dementia by using the neural network model for diagnosing the brain disease.

In the meantime, the processor 110 may predict a brain disease based on the information about at least one important image effective for diagnosing the brain disease selected through the foregoing embodiments. When the new medical image is input to the computing device 100 for diagnosing the brain disease, the processor 110 may select an important image in the new medical image based on the number information of the image previously acquired through the machine learning model, and determine whether the brain disease is present based on the selected image. Further, the processor 110 may parcellate the brain region existing in the new medical image through the neural network model, and determine whether the brain disease is present according to a predetermined condition based on information about the parcellated brain region. That is, the processor 110 may predict the brain disease by using the information about the important image (e.g., the image optimized for diagnosing the specific brain disease) previously determined through the machine learning model. Further, the processor 110 may also perform a selective analysis on the medical image that is input in real time, and predict the brain disease based on a result of the selective analysis. In this case, the neural network model used for predicting the brain disease may be trained based on at least one image selected as the image effective for diagnosing the brain disease.

According to the embodiment of the present disclosure, the memory 130 may store a predetermined type of information generated or determined by the processor 110 and a predetermined type of information received by a network unit 150.

According to the embodiment of the present disclosure, the memory 130 may include at least one type of storage medium among a flash memory type, a hard disk type, a multimedia card micro type, a card type of memory (for example, an SD or XD memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disk, and an optical disk. The computing device 100 may also be operated in relation to web storage performing a storage function of the memory 130 on the Internet. The description of the foregoing memory is merely illustrative, and the present disclosure is not limited thereto.

The network unit 150 according to the embodiment of the present disclosure may use a predetermined form of a publicly known wire/wireless communication system.

The network unit 150 may receive the medical image in which the organ of the body is expressed from a medical image photographing system. For example, the medical image in which the organ of the body is expressed may be data for training or data for inferring of the neural network model trained with the two-dimensional characteristic or the three-dimensional characteristic. The medical image in which the organ of the body is expressed may be the three-dimensional T1 MR image including at least one brain region. The medical image in which the organ of the body is expressed is not limited to the foregoing example, and may include all of the images, such as X-ray images and CT images, related to the organ of the body obtained through the photographing.

The network unit 150 may transceive information processed by the processor 110, the user interface, and the like through communication with other terminals. For example, the network unit 150 may provide the user interface generated by the processor 110 to a client (for example, a user terminal). Further, the network unit 150 may receive the external input of the user applied to the client and transfer the received external input to the processor 110. In this case, the processor 110 may process the operations of output, correction, change, addition, and the like of the information provided through the user interface based on the external input of the user received from the network unit 150.

In the meantime, the computing device 100 according to the embodiment of the present disclosure is a computing system for transceiving information with the client through communication and may be a server. In this case, the client may be a predetermined form of terminal accessible to the server. For example, the computing device 100 that is the server may receive a medical image from a medical image photographing terminal and predict disease, and provide the user terminal with the user interface including the predicted result. The user terminal may output the user interface received from the computing device 100 that is the server, and input or process information through interaction with the user.

In an additional embodiment, the computing device 100 may also include a predetermined form of terminal which receives data resources generated in a predetermined server and performs additional information processing.

Figure 2:
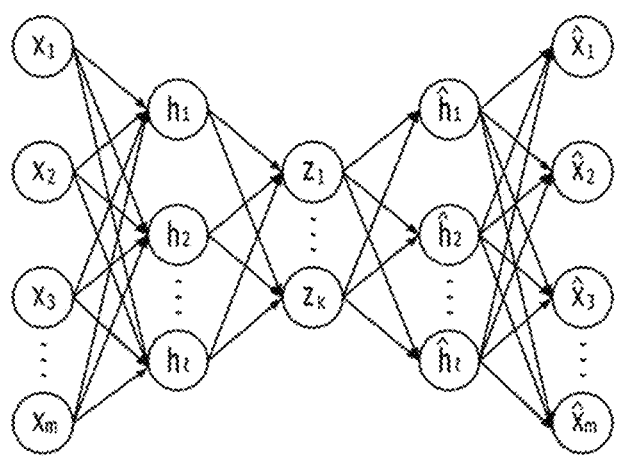
FIG. 2 is a schematic diagram illustrating a network function according to the embodiment of the present disclosure.

FIG. 2 is a schematic diagram illustrating a network function according to the embodiment of the present disclosure.

Throughout the present specification, the meanings of a calculation model, a nerve network, the network function, and the neural network may be interchangeably used. The neural network may be formed of a set of interconnected calculation units which are generally referred to as "nodes." The "nodes" may also be called "neurons." The neural network consists of one or more nodes. The nodes (or neurons) configuring the neural network may be interconnected by one or more links.

In the neural network, one or more nodes connected through the links may relatively form a relationship of an input node and an output node. The concept of the input node is relative to the concept of the output node, and a predetermined node having an output node relationship with respect to one node may have an input node relationship in a relationship with another node, and a reverse relationship is also available. As described above, the relationship between the input node and the output node may be generated based on the link. One or more output nodes may be connected to one input node through a link, and a reverse case may also be valid.

In the relationship between an input node and an output node connected through one link, a value of the output node data may be determined based on data input to the input node. Herein, a link connecting the input node and the output node may have a weight. The weight is variable, and in order for the neural network to perform a desired function, the weight may be varied by a user or an algorithm. For example, when one or more input nodes are connected to one output node by links, respectively, a value of the output node may be determined based on values input to the input nodes connected to the output node and weights set in the link corresponding to each of the input nodes.

As described above, in the neural network, one or more nodes are connected with each other through one or more links to form a relationship of an input node and an output node in the neural network. A characteristic of the neural network may be determined according to the number of nodes and links in the neural network, a correlation between the nodes and the links, and a value of the weight assigned to each of the links. For example, when there are two neural networks in which the numbers of nodes and links are the same and the weights between the links are different, the two neural networks may be recognized to be different from each other.

The neural network may consist of a set of one or more nodes. A subset of the nodes forming the neural network may form a layer. Some of the nodes configuring the neural network may form one layer based on distances from an initial input node. For example, a set of nodes having a distance of n from an initial input node may form n layers. The distance from the initial input node may be defined by the minimum number of links, which need to be passed from the initial input node to a corresponding node. However, the definition of the layer is arbitrary for the description, and a degree of the layer in the neural network may be defined by a different method from the foregoing method. For example, the layers of the nodes may be defined by a distance from a final output node.

The initial input node may mean one or more nodes to which data is directly input without passing through a link in a relationship with other nodes among the nodes in the neural network. Otherwise, the initial input node may mean nodes which do not have other input nodes connected through the links in a relationship between the nodes based on the link in the neural network. Similarly, the final output node may mean one or more nodes that do not have an output node in a relationship with other nodes among the nodes in the neural network. Further, the hidden node may mean nodes configuring the neural network, not the initial input node and the final output node.

In the neural network according to the embodiment of the present disclosure, the number of nodes of the input layer may be the same as the number of nodes of the output layer, and the neural network may be in the form that the number of nodes decreases and then increases again from the input layer to the hidden layer. Further, in the neural network according to another embodiment of the present disclosure, the number of nodes of the input layer may be smaller than the number of nodes of the output layer, and the neural network may be in the form that the number of nodes decreases from the input layer to the hidden layer. Further, in the neural network according to another embodiment of the present disclosure, the number of nodes of the input layer may be larger than the number of nodes of the output layer, and the neural network may be in the form that the number of nodes increases from the input layer to the hidden layer. The neural network according to another embodiment of the present disclosure may be the neural network in the form in which the foregoing neural networks are combined.

A deep neural network (DNN) may mean the neural network including a plurality of hidden layers, in addition to an input layer and an output layer. When the DNN is used, it is possible to recognize a latent structure of data. That is, it is possible to recognize latent structures of photos, texts, videos, voice, and music (for example, what objects are in the photos, what the content and emotions of the texts are, and what the content and emotions of the voice are). The DNN may include a convolutional neural network (CNN), a recurrent neural network (RNN), an auto encoder, Generative Adversarial Networks (GAN), a restricted Boltzmann machine (RBM), a deep belief network (DBN), a Q network, a U network Siamese network, and the like. The foregoing description of the deep neural network is merely illustrative, and the present disclosure is not limited thereto.

In the embodiment of the present disclosure, the network function may include an auto encoder. The auto encoder may be one type of artificial neural network for outputting output data similar to input data. The auto encoder may include at least one hidden layer, and the odd-numbered hidden layers may be disposed between the input/output layers. The number of nodes of each layer may decrease from the number of nodes of the input layer to an intermediate layer called a bottleneck layer (encoding), and then be expanded symmetrically with the decrease from the bottleneck layer to the output layer (symmetric with the input layer). The auto encoder may perform a nonlinear dimension reduction. The number of input layers and the number of output layers may correspond to the dimensions after preprocessing of the input data. In the auto encoder structure, the number of nodes of the hidden layer included in the encoder decreases as a distance from the input layer increases. When the number of nodes of the bottleneck layer (the layer having the smallest number of nodes located between the encoder and the decoder) is too small, the sufficient amount of information may not be transmitted, so that the number of nodes of the bottleneck layer may be maintained in a specific number or more (for example, a half or more of the number of nodes of the input layer and the like).

The neural network may be trained by at least one scheme of supervised learning, unsupervised learning, semi-supervised learning, and reinforcement learning. The training of the neural network may be a process of applying knowledge for the neural network to perform a specific operation to the neural network.

The neural network may be trained in a direction of minimizing an error of an output. In the training of the neural network, training data is repeatedly input to the neural network and an error of an output of the neural network for the training data and a target is calculated, and the error of the neural network is back-propagated in a direction from an output layer to an input layer of the neural network in order to decrease the error, and a weight of each node of the neural network is updated. In the case of the supervised learning, training data labeled with a correct answer (that is, labeled training data) is used, in each training data, and in the case of the unsupervised learning, a correct answer may not be labeled to each training data. That is, for example, the training data in the supervised learning for data classification may be data, in which category is labeled to each of the training data. The labeled training data is input to the neural network and the output (category) of the neural network is compared with the label of the training data to calculate an error. For another example, in the case of the unsupervised learning related to the data classification, training data that is the input is compared with an output of the neural network, so that an error may be calculated. The calculated error is back-propagated in a reverse direction (that is, the direction from the output layer to the input layer) in the neural network, and a connection weight of each of the nodes of the layers of the neural network may be updated according to the back propagation. A change amount of the updated connection weight of each node may be determined according to a learning rate. The calculation of the neural network for the input data and the back propagation of the error may configure a learning epoch. The learning rate is differently applicable according to the number of times of repetition of the learning epoch of the neural network. For example, at the initial stage of the learning of the neural network, a high learning rate is used to make the neural network rapidly secure performance of a predetermined level and improve efficiency, and at the latter stage of the learning, a low learning rate is used to improve accuracy.

In the training of the neural network, the training data may be generally a subset of actual data (that is, data to be processed by using the trained neural network), and thus an error for the training data is decreased, but there may exist a learning epoch, in which an error for the actual data is increased. Overfitting is a phenomenon, in which the neural network excessively learns training data, so that an error for actual data is increased. For example, a phenomenon, in which the neural network learning a cat while seeing a yellow cat cannot recognize cats, other than a yellow cat, as cats, is a sort of overfitting. Overfitting may act as a reason of increasing an error of a machine learning algorithm. In order to prevent overfitting, various optimizing methods may be used. In order to prevent overfitting, a method of increasing training data, a regularization method, a dropout method of inactivating a part of nodes of the network during the learning process, a method using a bath normalization layer, and the like may be applied.

Figure 3:
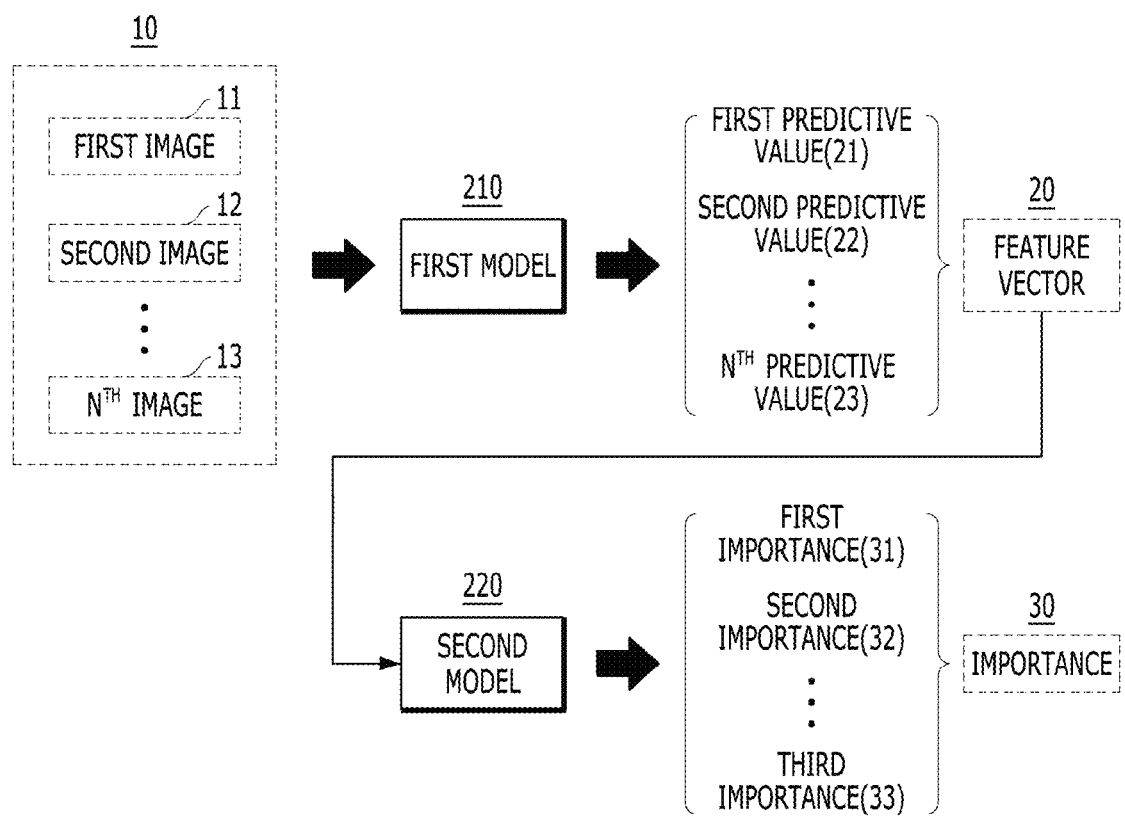
FIG. 3 is a block diagram illustrating an image selecting process for predicting disease of the computing device according to the embodiment of the present disclosure.
Figure 4:
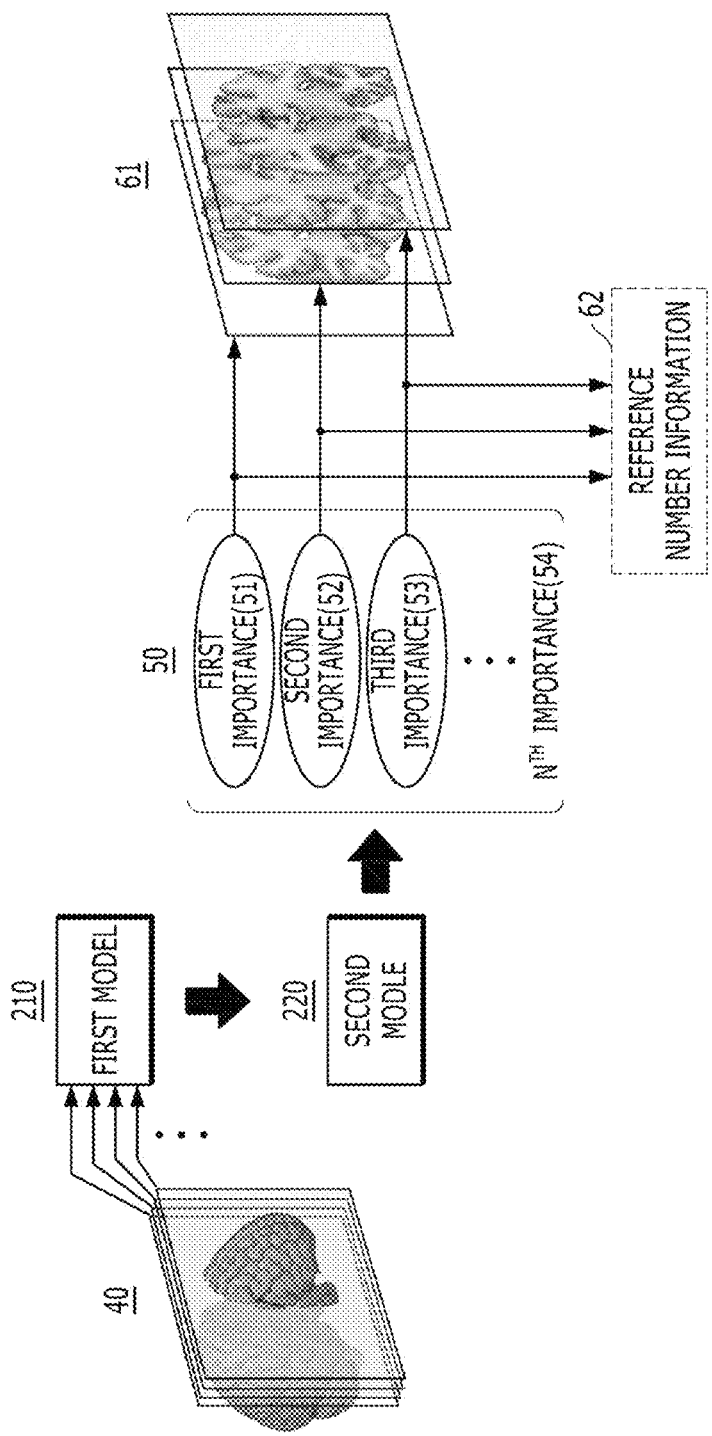
FIG. 4 is a conceptual diagram illustrating an image selecting process for predicting disease of the computing device according to the embodiment of the present disclosure.

FIG. 3 is a block diagram illustrating an image selecting process for predicting disease of the computing device according to the embodiment of the present disclosure. Further, FIG. 4 is a conceptual diagram illustrating an image selecting process for predicting disease of the computing device according to the embodiment of the present disclosure.

Referring to FIG. 3, the processor 110 of the computing device 100 according to the embodiment of the present disclosure may generate predictive values 21, 22, and 23 of a brain disease based on 2D medical images 11, 12, and 13 included in a 3D medical image 10 by using a pre-trained first model 210. In this case, the first model 210 may output the predictive values 21, 22, and 23 of the brain disease as one feature vector 20. The processor 110 may use each of the 2D medical images 11, 12, and 13 as an input of the first model 210. The processor 110 may generate the feature vector 20 including the predictive values 21, 22, and 23 of the brain disease for the 2D medical images 11, 12, 13, respectively, through the first model 210.

For example, the 3D medical image 10 may be a 3D MR image obtained by capture the entire brain region. The 2D medical images 11, 12, and 13 may be 2D slice images generated by processing the 3D MR image. The 2D medical images 11, 12, and 13 may be discriminated by number information according to an order or a location within the 3D medical image 10. The predictive values 21, 22, and 23 of the brain disease may be existence probability values of a specific disease, such as Alzheimer's dementia, corresponding to the 2D medical images 11, 12, 13, respectively, input to the first model 210.

The first model 210 may be a neural network model which receives at least a part of the 2D medical images 11, 12, and 13 generated from the 3D medical image 10 and estimates presence of the brain disease. The first model 210 may include a first neural network extracting features for predicting the brain disease from the input images (for example, the 2D medical images). Further, the first model 210 may include a second neural network outputting predictive values of the brain disease for each of the input images based on the features extracted by the first neural network and personal information and number information included in the input images.

For example, the first model 210 may include a first neural network that is a 2D convolution neural network which receives a medical image, such as a 2D slice image, and a second neural network that is a fully-connected neural network that receives output data of the first neural network. The first neural network may receive each of the 2D medical images 11, 12, and 13 configuring the 3D medical image 10 and extract a feature corresponding to each of the images 11, 12, and 13. The second neural network may output the predictive values 21, 22, and 23 for the presence of the specific disease, such as Alzheimer's dementia, based on the features corresponding to the respective images 11, 12, and 13, personal information, such as gender and age, of the image subject, and location information (or number information) of each of the images 11, 12, and 13.

Referring to FIG. 3, the processor 110 may calculate importance 30 of each of the 2D medical images 11, 12, and 13 based on the feature vector 20 including the predictive values 21, 22, and 23 of the brain disease by using the pre-trained second model 220. The importance 30 may be prediction accuracy representing how well each of the 2D medical images 11, 12, and 13 is suitable for predicting the brain disease. The importance 30 may include first importance 31, second importance 32, and $N^{th}$ importance 33 (N is a natural number) representing prediction accuracy of the 2D medical images 11, 12, and 13, respectively.

For example, the processor 110 may determine importance of the probability values corresponding to the 2D medical images 11, 12, and 13, respectively, by inputting the feature vector 20 including the presence probability values of the specific disease, such as Alzheimer's dementia, to the second model 220. In this case, the importance of each of the probability values may be used as an index for selecting images effective for predicting the specific disease, such as Alzheimer's dementia, among the 2D medical images 11, 12, and 13. That is, the importance may be an evaluation index representing accuracy of the brain disease prediction of each of the 2D medical images 11, 12, and 13.

The second model 220 may be a machine learning model which receives an output value of the first model 210 and determines whether the brain disease is present. The second model 220 may receive the feature vector 20 output from the first model 210 and determine whether the brain disease is present by using a tree boosting algorithm. The second model 220 may determine the importance 31, 32, and 33 of the features 21, 22, and 23 included in the feature vector 20 by using the characteristic of the tree boosting algorithm (for example, the XGboost algorithm) in the process of determining whether the brain disease is present.

The entire flow of the image selecting process by using the first model 210 and the second model 220 according to the embodiment of the present disclosure will be described in detail with reference to FIG. 4.

Referring to FIG. 4, the processor 110 may use each of the 2D slice images included in the 3D MR image 40 expressing the entire brain region as an input of the first model 210. In this case, the 2D slice images input to the first model 210 may also be all of the images configuring the 3D MR image 40, or some of them. The first model 210 may calculate a probability value of Alzheimer's dementia for each of the received 2D slice images, and generate one feature vector.

The processor 110 may use one feature vector generated through the first model 210 as the input of the second model 220. The second model 220 may calculate importance 50 corresponding to each of the features (e.g., the probability values of Alzheimer's dementia) included in one feature vector. For example, when N 2D slice images are input to the first model 210 and a feature vector including N features is generated, the second model 220 may output N importance 51, 52, 53, and 54 corresponding to the N images (N is a natural number).

The processor 110 may select at least one of the 2D slice images input to the first model 210 as an input image of the model for predicting the brain disease by comparing the N importance 51, 52, 53, and 54 output from the second model 220 with a threshold value. The processor 110 may compare the N importance 51, 52, 53, and 54 with the previously determined threshold value and select a 2D slice image corresponding to the importance having the threshold value or more as the input image of the model. For example, as illustrated in FIG. 4, the processor 110 may select the first importance 51, the second importance 52, and the third importance 53 having the threshold value or more, except for the $N^{th}$ importance 54 having a value less than the threshold value, among the N importance 51, 52, 53, and 54. The processor 110 may determine the three 2D slice images corresponding to the first importance 51, the second importance 52, and the third importance 53 having the threshold value or more as the input image of the model effective for predicting Alzheimer's dementia.

Further, in the foregoing process, the processor 110 may acquire number information indicating where the 2D slice image determined as the input image of the model is located in the 3D MR image. For example, when the 3D MR image is divided into L 2D slice images, L number information representing the locations in the 3D MR image may be sequentially assigned to the L 2D slice images (L is a natural number). The processor 110 may acquire number information corresponding to the input image of the model based on the L number information. The processor 110 may use the number information corresponding to the input image of the model as reference number information for selecting new 2D medical images received for diagnosing the brain disease. As illustrated in FIG. 4, in the case where the processor 110 determines three 2D slice images 61 corresponding to the three importance 51, 52, and 53 as the input images of the model, the processor 110 may store the number information of the three 2D slice images 61 in the memory 130 as reference number information 62 and use the stored number information for selecting subsequent images.

In the meantime, the processor 110 may use at least one image suitable for predicting the brain disease selected based on the output of the second model 220 as training data of the neural network model performing the prediction of the brain disease like the first model 210. For example, in the case where the three 2D slice images 61 are selected as illustrated in FIG. 4, the processor 110 may train the neural network model that calculates a probability value of Alzheimer's dementia based on the three 2D slice images 61. That is, the processor 110 may establish training data with high purity for the model for predicting Alzheimer's dementia by removing the images unnecessary (unsuitable) for predicting Alzheimer's dementia among the 2D slice images included in the 3D MR image. Through the training data with high purity established by the processor 110, the neural network model may considerably improve training efficiency and prediction accuracy for predicting Alzheimer's dementia.

Figure 5:
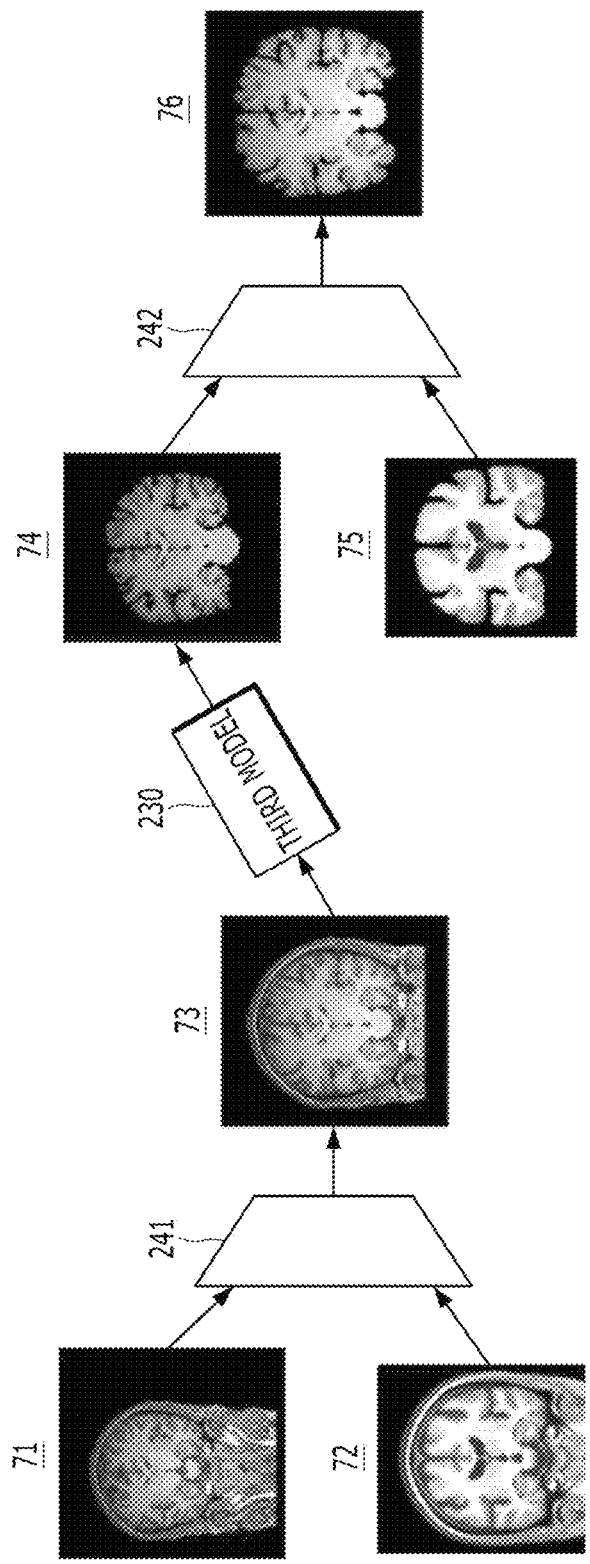
FIG. 5 is a conceptual diagram illustrating a pre-processing process for a medical image of the computing device according to the embodiment of the present disclosure.

FIG. 5 is a conceptual diagram illustrating a pre-processing process for a medical image of the computing device according to the embodiment of the present disclosure.

Referring to FIG. 5, the processor 110 may extract a brain parenchyma region from the medical image by using a pre-trained third model 230 for the purpose of removing tissue that interferes with the analysis of brain disease from a medical image. In this case, the third model 230 may a neural network model which receives the 2D medical image including at least one brain region, removes a region other than the brain, and extracts a brain parenchyma region. The processor 110 may use the 2D medical images including the brain parenchyma region extracted through the third model 230 as an input of the first model 210. Through this, performance of the image selection using the first model 210 and the second model 220 and performance of the diagnosis of the brain disease using the first model 210 may be improved.

For example, the processor 110 may convert a 2D medical image 71 including at least one brain region based on a first template 72. The processor 110 may perform primary rigid transform 241 based on the first template 72 representing a reference location of the brain region and the 2D medical image 71. Through this, the processor 110 may generate an image 73 in which the brain regions are aligned based on the first template 72. The processor 110 may extract a brain parenchyma region in the image 73 in which the brain regions are aligned by using the third model 230, and generate an image 74 in which the brain parenchyma region is extracted. The processor 110 may convert the image 74 in which the brain parenchyma region is extracted based on a second template 75. The processor 110 may perform secondary rigid transform 242 based on the second template 75 representing the reference location of the brain parenchyma region and the image 74 in which the brain parenchyma region is extracted. Through this, the processor 110 may generate the image 76 in which the brain parenchyma regions are aligned based on the second template 75. The processor 110 may use the image 76 in which the brain parenchyma regions are aligned as an input of the first model 210.

Figure 6:
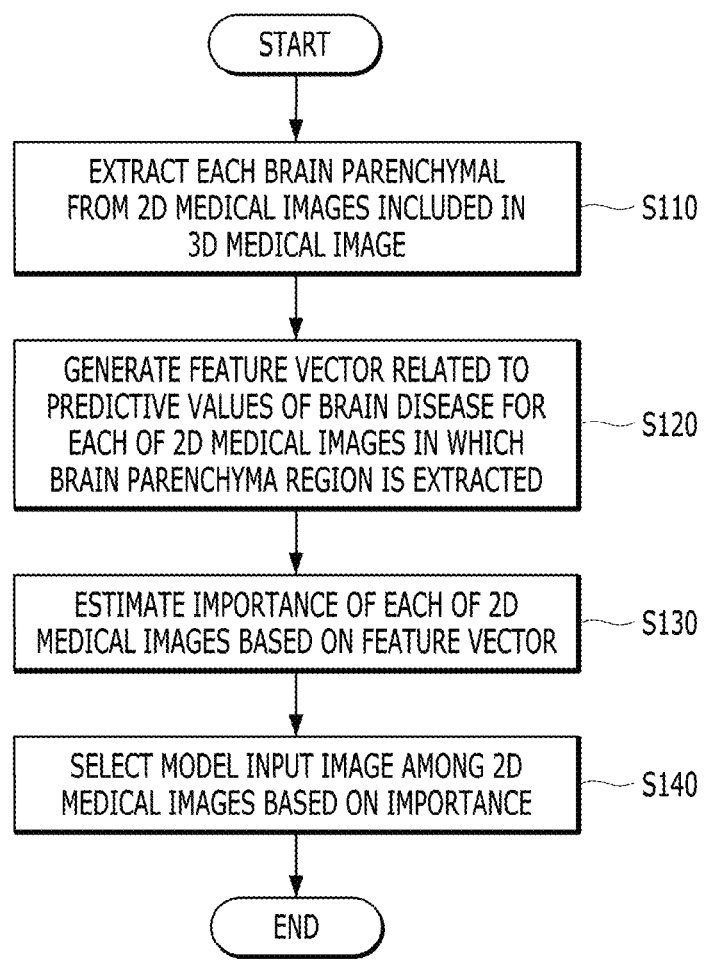
FIG. 6 is a flowchart illustrating a method of selecting an image for predicting disease according to an embodiment of the present disclosure.

FIG. 6 is a flowchart illustrating a method of selecting an image for predicting disease according to an embodiment of the present disclosure.

Referring to FIG. 6, in operation S110, the computing device 100 may receive a medical image for predicting a brain disease from a medical image photographing system. The medical image for predicting the brain disease may also be a 3D MR image, and 2D slice images configuring the 3D MR image. When the computing device 100 receives the 3D MR image as the medical image, the computing device 100 may generate 2D slice images by processing the 3D MR image. When the computing device 100 receives the 2D slice images as the medical image, the computing device 100 may use the 2D slice images as an input of a first model for selecting an image or diagnosing the brain disease without separate processing for the received medical image.

In operation S110, the computing device 100 may extract a brain parenchyma region in which other tissues, such as bones, are removed from the 2D slice images. The computing device 100 may perform pre-processing for removing regions unnecessary for determining the brain disease on the 2D slice images before the input of the 2D slice images to the first model. The computing device 100 may perform primary transform of assigning the brain regions included in the 2D slice images based on a template representing a reference location of the entire brain region. The computing device 100 may extract the brain parenchyma region from the primarily converted images by using a third model. The computing device 100 may perform secondary transform of aligning the extracted brain parenchyma regions based on the template representing a reference location of the brain parenchyma region. Through the foregoing process, the input image of the first model for selecting an image or diagnosing the brain disease may be generated.

In operation S120, the computing device 100 may generate a feature vector including predictive values of the brain disease for each of the images in which the brain parenchyma region is extracted by using the first model including a neural network model. For example, the computing device 100 may calculate a presence probability value of Alzheimer's dementia corresponding to each of the 2D slice images in which the brain parenchyma region is extracted by using the first model including the neural network model. The computing device 100 may generate the feature vector including the presence probability value of Alzheimer's dementia based on the 2D slice images in which the brain parenchyma region is extracted, personal information of an image photographing target labeled to each image, and location information within the 3D image.

In operation S130, the computing device 100 may estimate importance of each of the images in which the brain parenchyma region is extracted based on the feature vector that is the output of the first model by using a second model that uses a tree boosting algorithm. The importance may be an index for evaluating how suitable or effective each image is for predicting the brain disease. For example, the computing device 100 may derive importance representing accuracy of the presence probability values of Alzheimer's dementia included in the feature vector by using the second model that is the XGboost model. The XGboost model referred to as the second model is merely one example of a tree boosting algorithm model, and is not limited thereto.

In operation S140, the computing device 100 may select an image suitable for predicting the brain disease among the 2D medical images in which the brain parenchyma region is extracted based on the importance that is the output of the second model. The computing device 100 may select images effective for predicting the brain disease by comparing the importance of each image with a threshold value. For example, the computing device 100 may select all of the images corresponding to the importance having the threshold value or more as a model input image effective for predicting Alzheimer's dementia. Further, the computing device 100 may also select an image corresponding to the largest value among the importance having the threshold value or more as the model input image effective for predicting Alzheimer's dementia.

In operation S140, the computing device 100 may acquire and store number information about the model input images selected to be suitable for predicting the brain disease. In this case, the number information may be information indicating where the model input images corresponding to the 2D slice images are located in the 3D MR image. For example, the computing device 100 may acquire number information of the model input images effective for predicting Alzheimer's dementia. The computing device 100 may store the acquired number information as reference number information. The computing device 100 may use the reference number information for selecting a new 2D slice image suitable as the input to the neural network model (for example, the first model) for predicting Alzheimer's dementia. Through the process, the computing device 100 may effectively perform the prediction of the brain disease by selecting the medical images appropriate to the type of brain disease.

In the meantime, in operation S140, the computing device 100 may configure a training data set of the disease prediction model based on the model input images selected to be suitable for predicting the brain disease. The computing device 100 may train the model by inputting the training data set consisting of the images selected based on the importance representing the accuracy of the prediction of the brain disease to the disease prediction model. The computing device 100 may accurately estimate the brain disease based on the medical image by using the disease prediction model trained based on the model input images suitable for predicting the brain disease.

Figure 7:
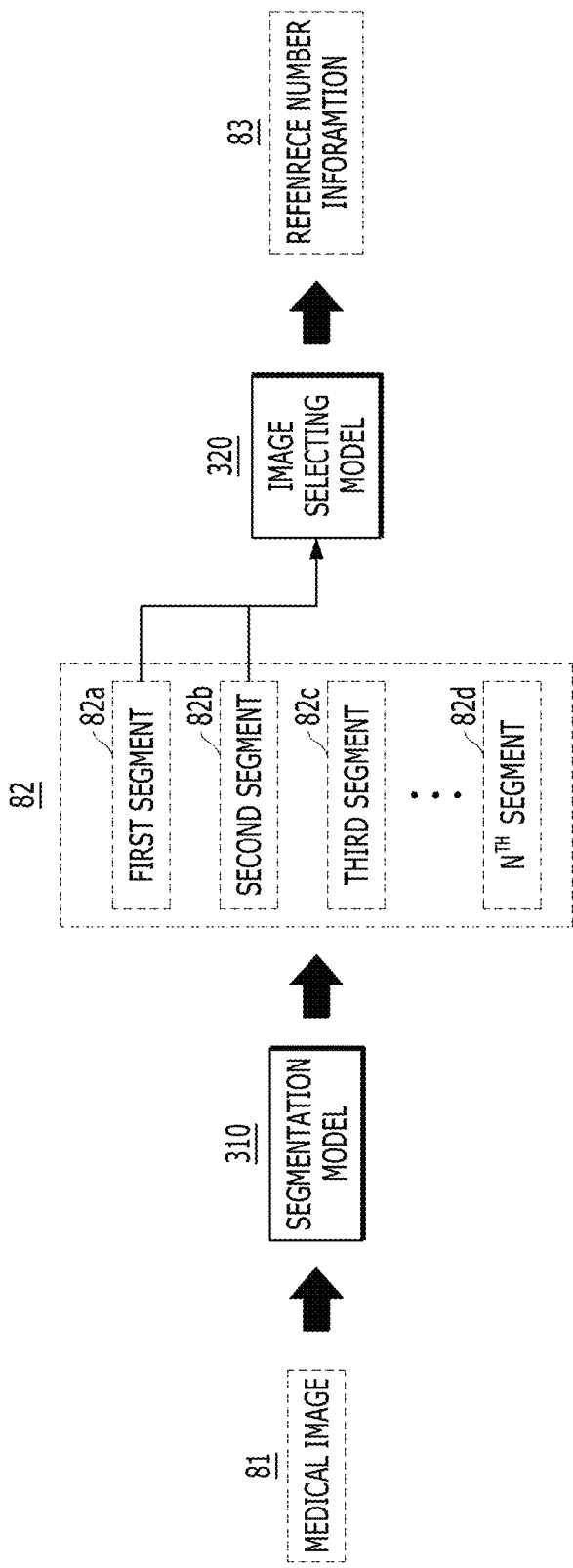
FIG. 7 is a block diagram illustrating an image selecting process for predicting disease of the computing device according to an alternative embodiment of the present disclosure.

FIG. 7 is a block diagram illustrating an image selecting process for predicting disease of the computing device according to an alternative embodiment of the present disclosure.

Referring to FIG. 7, the processor 110 of the computing device 100 according to an alternative embodiment of the present disclosure may parcellate at least one brain region existing in a 2D medical image 81 included in a 3D medical image by using a pre-trained segmentation model 310 into detailed regions. The segmentation model 310 may receive a 2D medical image 81 and generate output data 82 including a plurality of segments 82a, 82b, 82c, and 882d representing detailed regions of the brain, respectively.

For example, the segmentation model 310 may parcellate the brain region into a cortex region and detailed regions including cortex lower regions based on the 2D medical image 30 representing the entire brain region. The first segment 82a may be data representing a hippocampus. The second segment 82b may be data representing an amygdala. The third segment 82c may be data representing cortex. The $N^{th}$ segment 82d may be data representing ventricle. The third segment 82c may include sub-segments representing an entorhinal cortex and a parahippocampal cortex, respectively. The particular description of each of the segments 82a, 82b, 82c, and 82d is merely one example, and the order and the content thereof may vary according to the segmentation result.

The processor 110 may select at least one model input image suitable for predicting the brain disease among the 2D medical images based on the information about the brain region extracted through the segmentation model 310. The processor 110 may select at least one image satisfying a predetermined condition related to a reference region among the 2D medical images as the model input image based on the output data 82 of the segmentation model 310. The reference region may be the brain region representing the structure for determining the specific brain disease. The processor 110 may select a 2D medical image (e.g., the image effective for predicting the specific brain disease) that represents the reference region well by determining whether a predetermined condition is satisfied based on some of the information about the brain detailed regions. In this case, the processor 110 may use an image selection model 320 for determining whether the predetermined condition is satisfied based on some of the information about the brain detailed regions.

For example, the processor 110 may select a model input image suitable for determining Alzheimer's dementia by using location information of at least one of the segments 82a, 82b, 82c, and 82d in the 2D slice image 82 parcellated through the segmentation model 310. The processor 110 may acquire number information 83 of the 2D slice image which best presents a medial temporal lobe that is the reference region based on the information about the brain detailed regions, such as hippocampus, amygdala, olfactory cortex, parahippocampal cortex, and ventricle, by using the image selection model 320. The processor 110 may comprehensively use all of the segments 82a, 82b, 82c, and 82d for determining whether a predetermined condition is satisfied. Depending on the case, as illustrated in FIG. 7, the processor 110 may also use only the segments 82a and 82b required for determining whether the predetermined condition is satisfied.

The condition for determining the 2D slice image which best represents the reference region may be previously set based on the location information of at least one of the segments 82a, 82b, 82c, and 82d. In particular, when the predetermined condition for determining the 2D slice image corresponding to the center of mass of the third ventricle as the model input image is set in advance, the processor 110 may select an image corresponding to the center of mass of the third ventricle among the 2D slice images included in the 3D MR image as the model input image for determining Alzheimer's dementia. In this case, the processor 110 may determine number information indicating the position of the model input image within the 3D MR image as the reference number information 83. The processor 110 may use the reference number information 83 for extracting the 2D slice image effective for determining Alzheimer's dementia in the 3D MR image itself.

In the meantime, the processor 110 according to an alternative embodiment of the present disclosure may use at least one image suitable for predicting the brain disease selected based on the predetermined condition as training data of the neural network model performing the prediction of the brain disease.

Figure 8:
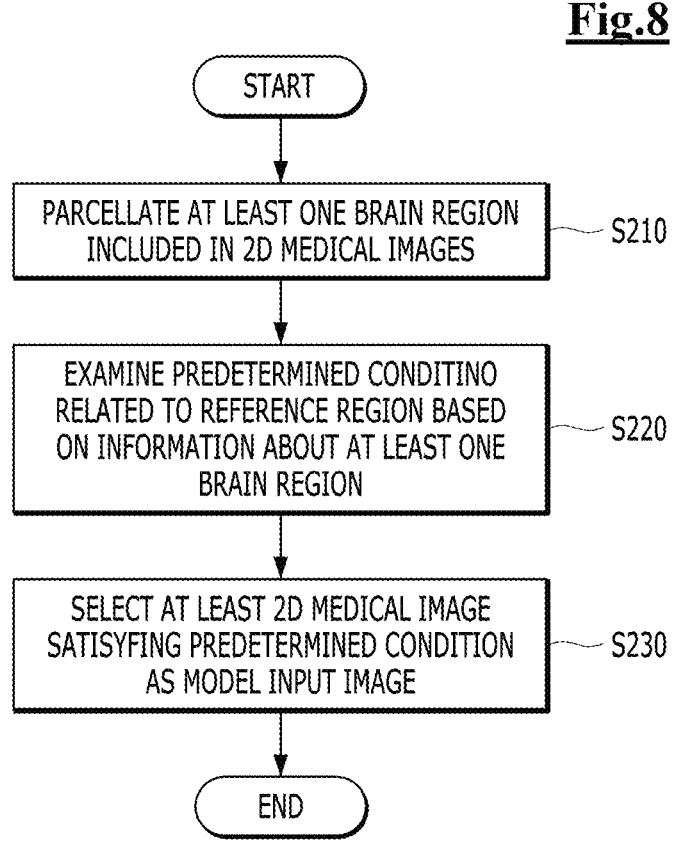
FIG. 8 is a flowchart illustrating a method of selecting an image for predicting disease according to an alternative embodiment of the present disclosure.

FIG. 8 is a flowchart illustrating a method of selecting an image for predicting disease according to an alternative embodiment of the present disclosure.

Referring to FIG. 8, in operation S210, the computing device 100 may receive a medical image for predicting a brain disease from a medical image photographing system. The medical image for predicting the brain disease may also be a 3D MR image, and 2D slice images configuring the 3D MR image. When the computing device 100 receives the 3D MR image as the medical image, the computing device 100 may generate 2D slice images by processing the 3D MR image. When the computing device 100 receives the 2D slice images as the medical image, the computing device 100 may use the 2D slice images as an input of a segmentation model which parcellates a brain region into detailed regions without separate processing for the received medical image.

In operation S210, the computing device 100 may parcellate at least one brain region included in the 2D slice images by using the segmentation model. The computing device 100 may parcellate the brain detailed regions in accordance with the brain region included in the 2D slice images by using the segmentation model, and extract information about each of the detailed regions. The computing device 100 may also use the 3D MR image itself, not the 2D slice images, as the input of the segmentation model. In this case, the computing device 100 may parcellate the entire brain region expressed in 3D into respective detailed regions by using the segmentation model.

In operation S220, the computing device 100 may examine a predetermined condition related to the reference region based on information about the brain detailed regions. For example, the computing device 100 may examine whether information about the brain detailed region that best represents a reference region for determining Alzheimer's dementia is included in each of the 2D slice images. The computing device 100 may also examine a location of the 3D MR image at which information about the brain detailed region that best represents a reference region for determining Alzheimer's dementia is included. In this case, the information about the brain detailed region may include location information of brain tissues, such as hippocampus, amygdala, olfactory cortex, parahippocampal cortex, and ventricle. The reference region for determining Alzheimer's dementia may be the central temporal lobe of the brain. Alzheimer's dementia is simply one example of the brain disease, and the type and the condition of the information may vary depending on the type of brain disease.

In operation S230, the computing device 100 may determine a model input image based on information about the 2D slice image satisfying a predetermined condition related to the reference region. The computing device 100 may select the image including location information of the brain tissue that best represents the reference region among the 2D slice images included in the 3D MR image as the model input image. Further, the computing device 100 may also extract the 2D slice image from the 3D MR image based on number information of the 2D slice image determined as the model input image. For example, when the previously determined predetermined condition for diagnosing Alzheimer's dementia is the center of mass of the third ventricle that best represents the central temporal lobe, the computing device 100 may select the 2D slice image itself corresponding to the center of mass of the third ventricle as the model input image. Further, the computing device 100 may also use the 2D slice image from the 3D MR image based on the number information of the 2D slice image corresponding to the center of mass of the third ventricle as the model input image. Through the process, the computing device 100 may effectively perform the prediction of the brain disease by selecting the medical images appropriate to the type of brain disease.

In the meantime, in operation S230, the computing device 100 may configure a training data set of a disease prediction model based on the model input images selected to be suitable for predicting the brain disease. The computing device 100 may train the model by inputting the training data set consisting of the images selected according to the predetermined condition to the disease prediction model. The computing device 100 may accurately estimate the brain disease based on the medical image by using the disease prediction model trained based on the model input images suitable for predicting the brain disease.

Figure 9:
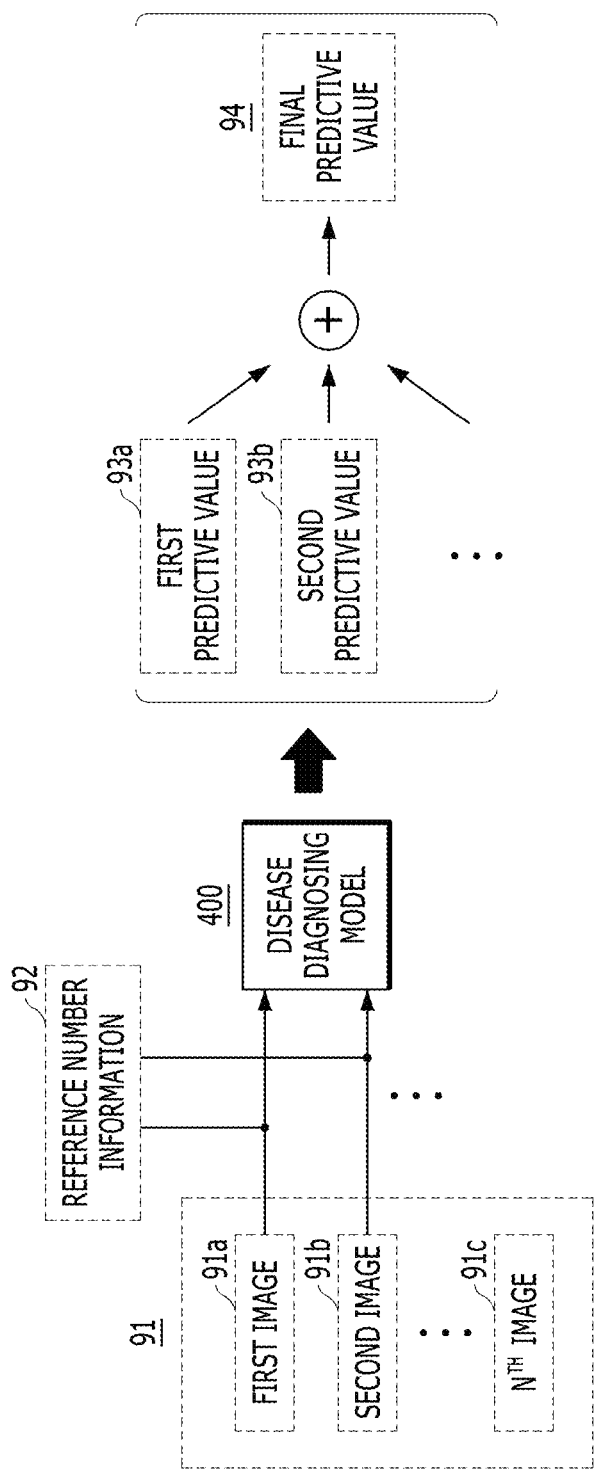
FIG. 9 is a block diagram illustrating a process of predicting disease of the computing device according to the alternative embodiment of the present disclosure.

FIG. 9 is a block diagram illustrating a process of predicting disease of the computing device according to the alternative embodiment of the present disclosure.

Referring to FIG. 9, the processor 110 of the computing device 100 according to the embodiment of the present disclosure may extract a brain parenchyma region from a medical image by using a pre-trained pre-processing model for the purpose of removing tissue that interferes with the analysis of brain disease from a medical image. In this case, the pre-processing model may a neural network model which receives the 2D medical image including at least one brain region, removes a region other than the brain, and extracts a brain parenchyma region. The processor 110 may use the 2D medical images including the brain parenchyma region extracted through the pre-processing model for a selection process for inputting of a disease diagnosing model 400. The method of extracting the brain parenchyma region by using the pre-processing model is similar to that using the third model 230 (see FIG. 5), so that additional descriptions for the structure, operation, function, and the like of the model will be omitted.

The processor 110 may select at least one model input image (e.g., an input image of the disease diagnosing model 400) suitable for predicting the brain disease among 2D medical images 91 in which the brain parenchyma regions are extracted. In this case, the processor 110 may use any one of a method of using reference number information 92 previously acquired for selecting the model input image, and a method of calculating the reference number information 92 for each image. For example, the processor 110 may use a first image 91*a* and a second image 91*b* corresponding to the previously determined reference number information 92 as the model input image based on importance representing accuracy of the prediction of the brain disease. Further, the processor 110 may parcellate the 2D medical images 91 in which the brain parenchyma regions are extracted through the segmentation model, and determine or extract the first image 91a and the second image 91b corresponding to a predetermined condition as the model input images based on information about the parcellated 2D medical images.

As illustrated in FIG. 3, the processor 110 may determine the reference number information 92 in advance by using the second model 220 that calculate importance representing the accuracy of the prediction of the brain disease based on the outputs of the first model 210 and the second model 220 which receives all of the 2D medical images included in the 3D medical image and derive the predictive values of the brain disease. Herein, the reference number information 92 refers to location information of at least one 2D medical image of which importance is equal to or larger than a threshold value within the 3D medical image. The processor 110 may select and use images matched with the previously determined reference number information 92 as the input images of the disease diagnosing model 400 based on the first model 210 and the second model 220 among the new 2D medical images 91 in which the brain parenchyma regions are extracted. In this case, the disease diagnosing model 400 may be the same model of the first model 210 of FIG. 3.

As illustrated in FIG. 7, the processor 110 may parcellate the brain region included in the medical image by using the segmentation model 310 whenever the medical image is received. Further, the processor 110 may also acquire the reference number information 83 and 92 for the model image suitable for predicting the brain disease based on information about brain detailed regions parcellated by the segmentation model 310 by using the image selecting model 320. In this case, the image selecting model 320 may calculate the reference number information 83 and 92 based on information about the brain detailed regions corresponding to a predetermined condition related to a reference region. In this method, the processor 110 may use the 2D medical images 91a and 91b in which the brain parenchyma regions are extracted and which correspond to the reference number information 92 as the input of the disease diagnosing model 400 as it is. The processor 110 may also extract the 2D medical image corresponding to the reference number information 92 from the 3D medical image and use the extracted 2D medical image as the input of the disease diagnosing model 400.

Referring to FIG. 9, the processor 110 may predict a probability of presence of the brain disease based on at least one model input image by using the disease diagnosing model 400. For example, the processor 110 may acquire a first predictive value 93a and a second predictive value 93b corresponding to the input images 91a and 91b, respectively, by inputting the first image 91a and the second image 91b selected as described above to the disease diagnosing model 400. The processor 110 may calculate a final predictive value 94 by ensembling the first predictive value 93a and the second predictive value 93b estimated based on the input images 91a and 91b, respectively. Herein, the ensemble may mean the method of calculating the sum average of the respective predictive values, but is not limited thereto, and various ensemble methods may be applied. Through the process, the processor 110 does not provide unnecessary information for determining the brain disease and uses only the information effective for determining the brain disease, thereby significantly improving prediction performance of the brain disease.

In the meantime, the disease diagnosing model 400 may be pre-trained based on at least one image previously selected to be suitable for predicting the brain disease among the 2D medical images included in the 3D medical image by the processor 110. In this case, the input image for training the disease diagnosing model 400 may be at least one image suitable for predicting the brain disease selected by the computing device 100 through a process illustrated in FIG. 3 or 7. For example, the disease diagnosing model 400 may be trained based on at least one image selected based on the importance 30 representing accuracy of the prediction of the brain disease for each of the 2D medical images included in the 3D medical image through the first model 210 and the second model 220 of FIG. 3. The disease diagnosing model 400 may also be trained based on at least one image selected according to a predetermined reference from the 2D medical image 82 parcellated through the segmentation model 310 of FIG. 7. The training of the disease diagnosing model 400 based on the image selected through the process of FIG. 3 or 7 may greatly improve the whole training efficiency and prediction performance of the model compared to the training of the model based on all of the images.

Figure 10:
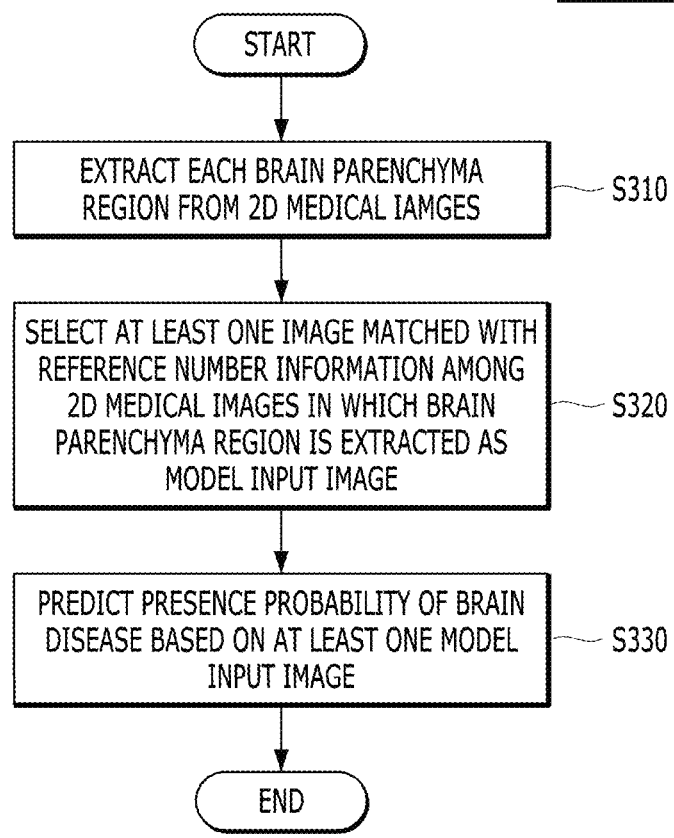
FIG. 10 is a flowchart illustrating a method of predicting disease based on a medical image according to an embodiment of the present disclosure.

FIG. 10 is a flowchart illustrating a method of predicting disease based on a medical image according to an embodiment of the present disclosure. The following process referring to FIG. 10 is one example of a method of selecting a medical image by using reference number information determined through a pre-calculation and determining a brain disease based on the selected image.

Referring to FIG. 10, in operation S310, the computing device 100 may receive a medical image for predicting a brain disease from a medical image photographing system. The medical image for predicting the brain disease may also be a 3D MR image, and 2D slice images configuring the 3D MR image. When the computing device 100 receives the 3D MR image as the medical image, the computing device 100 may generate 2D slice images by processing the 3D MR image. When the computing device 100 receives the 2D slice images as the medical image, the computing device 100 may use the 2D slice images as an input of a segmentation model which parcellates a brain region into detailed regions without separate processing for the received medical image.

In operation S310, the computing device 100 may extract a brain parenchyma region from each of the 2D medical images by using the pre-processing model. The brain parenchyma region refers to a region of the brain tissue excluding other tissues such as bones that interfere with the determination of brain disease. The computing device 100 may effectively perform the following operations for diagnosing the disease by generating the 2D medical image in which the brain parenchyma region is extracted.

In operation S320, the computing device 100 may select at least one 2D medical image matched to the previously determined reference number information as a model input image through the machine learning model. For example, the computing device 100 may extract location information of at least one 2D slice image suitable for predicting Alzheimer's dementia in advance based on importance of the prediction of Alzheimer's dementia for each of the 2D slice images included in the 3D MR images by using the machine learning models. The location information is the reference number information and is information indicating where the 2D slice image is located in the 3D MR image. The computing device 100 may select 2D slice images corresponding to the reference number information among the 2D slice images in which the brain parenchyma regions are extracted and use the selected 2D slice images as the input images of the model for diagnosing Alzheimer's dementia.

In operation S330, the computing device 100 may predict a probability of presence of the brain disease based on at least one 2D medical image selected according to the reference number information by using the disease diagnosing model. For example, the computing device 100 may input at least one 2D slice image selected according to the reference number information to the disease diagnosing model and output a probability value of the presence of Alzheimer's dementia corresponding to the 2D slice image. When the plurality of 2D slice images is input to the disease diagnosing model, the computing device 100 may generate a final predictive value by ensembling the probability values of the presence of Alzheimer's dementia corresponding to the respective images. The final predictive value is the information indicating the presence or absence of the brain disease determined based on the probability of the presence of the brain disease. Therefore, the computing device 100 may generate and provide information indicating whether Alzheimer's dementia is present through the disease diagnosing model.

Figure 11:
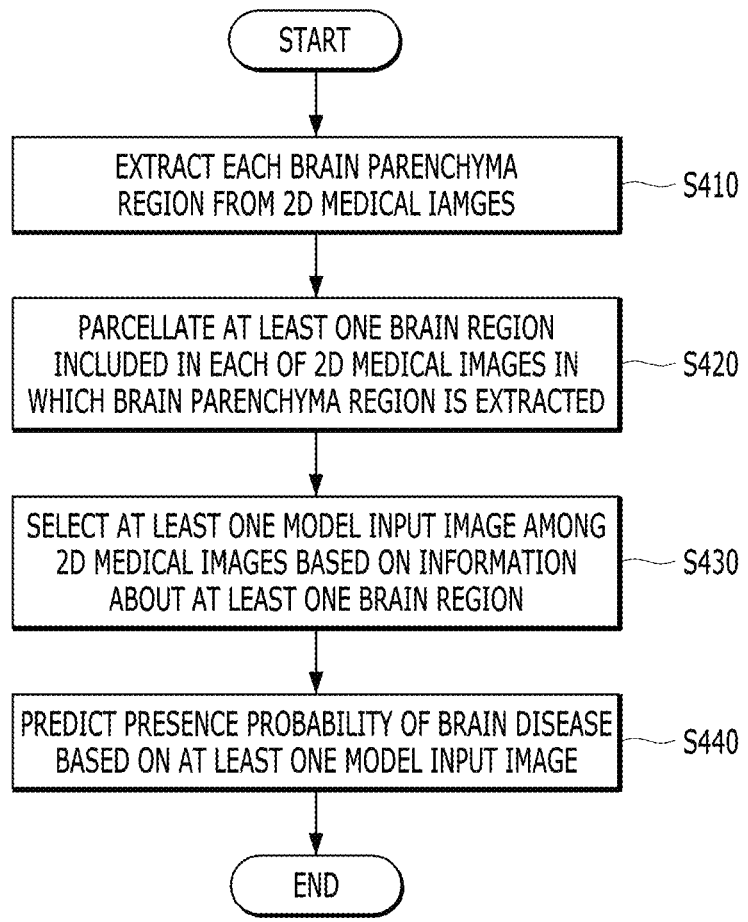
FIG. 11 is a flowchart illustrating a method of predicting disease based on a medical image according to an alternative embodiment of the present disclosure.

FIG. 11 is a flowchart illustrating a method of predicting disease based on a medical image according to an alternative embodiment of the present disclosure. The following process referring to FIG. 11 is an example of a method of extracting reference number information whenever a medical image is received, selecting an input image based on the reference number information, and determining a brain disease. The descriptions of operation S410 and operation S440 of FIG. 11 performing the same functions as those of operation S310 and operation S330 of FIG. 10 will be omitted.

Referring to FIG. 11, in operation S420, the computing device 100 may parcellate at least one brain region included in each of the 2D medical images in which the brain parenchyma regions are extracted into detailed regions by using the segmentation model. For example, the computing device 100 may discriminate the brain regions included in the 2D slice images in which the brain parenchyma regions are extracted into detailed regions, such as hippocampus, amygdala, olfactory cortex, parahippocampal cortex, and ventricle, by using the segmentation model and extract the detailed regions. In this case, the segmentation model may parcellate the detailed regions existing in each of the 2D slice images. When the ventricle region does not exist in the 2D slice image, the segmentation model may parcellate the 2D slice image into the remaining detailed regions excluding the ventricle region.

In operation S430, the computing device 100 may select at least one image suitable for predicting the brain disease among the 2D medical images as a model input image based on information about the brain detailed regions extracted through the segmentation model. In this case, the computing device 100 may acquire number information of at least one image suitable for predicting the brain disease as reference number information for selecting the model input image. For example, the computing device 100 may select the image including information about the brain detailed region corresponding to a predetermined condition as an image suitable for determining Alzheimer's dementia, and extract number information of the corresponding image. In this case, the predetermined condition is a previously determined value, and is a condition for determining whether the 2D slice image includes location information of the brain detailed region that best represents the central temporal lobe, which is the reference region required for determining Alzheimer's dementia. The computing device 100 may select the 2D slice image including location information (for example, the center of mass) of the brain detailed region (for example, the third ventricle) that best represents the central temporal lobe as the model input image according to the predetermined condition.

In the meantime, according to an embodiment of the present disclosure, a computer readable medium storing a data structure is disclosed.

The data structure may refer to organization, management, and storage of data that enable efficient access and modification of data. The data structure may refer to organization of data for solving a specific problem (for example, data search, data storage, and data modification in the shortest time). The data structure may also be defined with a physical or logical relationship between the data elements designed to support a specific data processing function. A logical relationship between data elements may include a connection relationship between user defined data elements. A physical relationship between data elements may include an actual relationship between the data elements physically stored in a computer readable storage medium (for example, a permanent storage device). In particular, the data structure may include a set of data, a relationship between data, and a function or a command applicable to data. Through the effectively designed data structure, the computing device may perform a calculation while minimally using resources of the computing device. In particular, the computing device may improve efficiency of calculation, reading, insertion, deletion, comparison, exchange, and search through the effectively designed data structure.

The data structure may be divided into a linear data structure and a non-linear data structure according to the form of the data structure. The linear data structure may be the structure in which only one data is connected after one data. The linear data structure may include a list, a stack, a queue, and a deque. The list may mean a series of dataset in which order exists internally. The list may include a linked list. The linked list may have a data structure in which data is connected in a method in which each data has a pointer and is linked in a single line. In the linked list, the pointer may include information about the connection with the next or previous data. The linked list may be expressed as a single linked list, a double linked list, and a circular linked list according to the form. The stack may have a data listing structure with limited access to data. The stack may have a linear data structure that may process (for example, insert or delete) data only at one end of the data structure. The data stored in the stack may have a data structure (Last In First Out, LIFO) in which the later the data enters, the sooner the data comes out. The queue is a data listing structure with limited access to data, and may have a data structure (First In First Out, FIFO) in which the later the data is stored, the later the data comes out, unlike the stack. The deque may have a data structure that may process data at both ends of the data structure.

The non-linear data structure may be the structure in which the plurality of pieces of data is connected after one data. The non-linear data structure may include a graph data structure. The graph data structure may be defined with a vertex and an edge, and the edge may include a line connecting two different vertexes. The graph data structure may include a tree data structure. The tree data structure may be the data structure in which a path connecting two different vertexes among the plurality of vertexes included in the tree is one. That is, the tree data structure may be the data structure in which a loop is not formed in the graph data structure.

Throughout the present specification, a calculation model, a nerve network, the network function, and the neural network may be used with the same meaning. Hereinafter, the terms of the calculation model, the nerve network, the network function, and the neural network are unified and described with a neural network. The data structure may include a neural network. Further, the data structure including the neural network may be stored in a computer readable medium. The data structure including the neural network may also include preprocessed data for processing by the neural network, data input to the neural network, a weight of the neural network, a hyper-parameter of the neural network, data obtained from the neural network, an active function associated with each node or layer of the neural network, and a loss function for training of the neural network. The data structure including the neural network may include predetermined configuration elements among the disclosed configurations. That is, the data structure including the neural network may include the entirety or a predetermined combination of pre-processed data for processing by neural network, data input to the neural network, a weight of the neural network, a hyper parameter of the neural network, data obtained from the neural network, an active function associated with each node or layer of the neural network, and a loss function for training the neural network. In addition to the foregoing configurations, the data structure including the neural network may include predetermined other information determining a characteristic of the neural network. Further, the data structure may include all type of data used or generated in a computation process of the neural network, and is not limited to the foregoing matter. The computer readable medium may include a computer readable recording medium and/or a computer readable transmission medium. The neural network may be formed of a set of interconnected calculation units which are generally referred to as "nodes." The "nodes" may also be called "neurons." The neural network consists of one or more nodes.

The data structure may include data input to the neural network. The data structure including the data input to the neural network may be stored in the computer readable medium. The data input to the neural network may include training data input in the training process of the neural network and/or input data input to the training completed neural network. The data input to the neural network may include data that has undergone pre-processing and/or data to be pre-processed. The pre-processing may include a data processing process for inputting data to the neural network. Accordingly, the data structure may include data to be pre-processed and data generated by the pre-processing. The foregoing data structure is merely an example, and the present disclosure is not limited thereto.

The data structure may include a weight of the neural network. (in the present specification, weights and parameters may be used with the same meaning.) Further, the data structure including the weight of the neural network may be stored in the computer readable medium. The neural network may include a plurality of weights. The weight is variable, and in order for the neural network to perform a desired function, the weight may be varied by a user or an algorithm. For example, when one or more input nodes are connected to one output node by links, respectively, the output node may determine a data value output from the output node based on values input to the input nodes connected to the output node and the weight set in the link corresponding to each of the input nodes. The foregoing data structure is merely an example, and the present disclosure is not limited thereto.

For a non-limited example, the weight may include a weight varied in the neural network training process and/or the weight when the training of the neural network is completed. The weight varied in the neural network training process may include a weight at a time at which a training cycle starts and/or a weight varied during a training cycle. The weight when the training of the neural network is completed may include a weight of the neural network completing the training cycle. Accordingly, the data structure including the weight of the neural network may include the data structure including the weight varied in the neural network training process and/or the weight when the training of the neural network is completed. Accordingly, it is assumed that the weight and/or a combination of the respective weights are included in the data structure including the weight of the neural network. The foregoing data structure is merely an example, and the present disclosure is not limited thereto.

The data structure including the weight of the neural network may be stored in the computer readable storage medium (for example, a memory and a hard disk) after undergoing a serialization process. The serialization may be the process of storing the data structure in the same or different computing devices and converting the data structure into a form that may be reconstructed and used later. The computing device may serialize the data structure and transceive the data through a network. The serialized data structure including the weight of the neural network may be reconstructed in the same or different computing devices through deserialization. The data structure including the weight of the neural network is not limited to the serialization. Further, the data structure including the weight of the neural network may include a data structure (for example, in the non-linear data structure, B-Tree, Trie, m-way search tree, AVL tree, and Red-Black Tree) for improving efficiency of the calculation while minimally using the resources of the computing device. The foregoing matter is merely an example, and the present disclosure is not limited thereto.

The data structure may include a hyper-parameter of the neural network. The data structure including the hyper-parameter of the neural network may be stored in the computer readable medium. The hyper-parameter may be a variable varied by a user. The hyper-parameter may include, for example, a learning rate, a cost function, the number of times of repetition of the training cycle, weight initialization (for example, setting of a range of a weight value to be weight-initialized), and the number of hidden units (for example, the number of hidden layers and the number of nodes of the hidden layer). The foregoing data structure is merely an example, and the present disclosure is not limited thereto.

Figure 12:
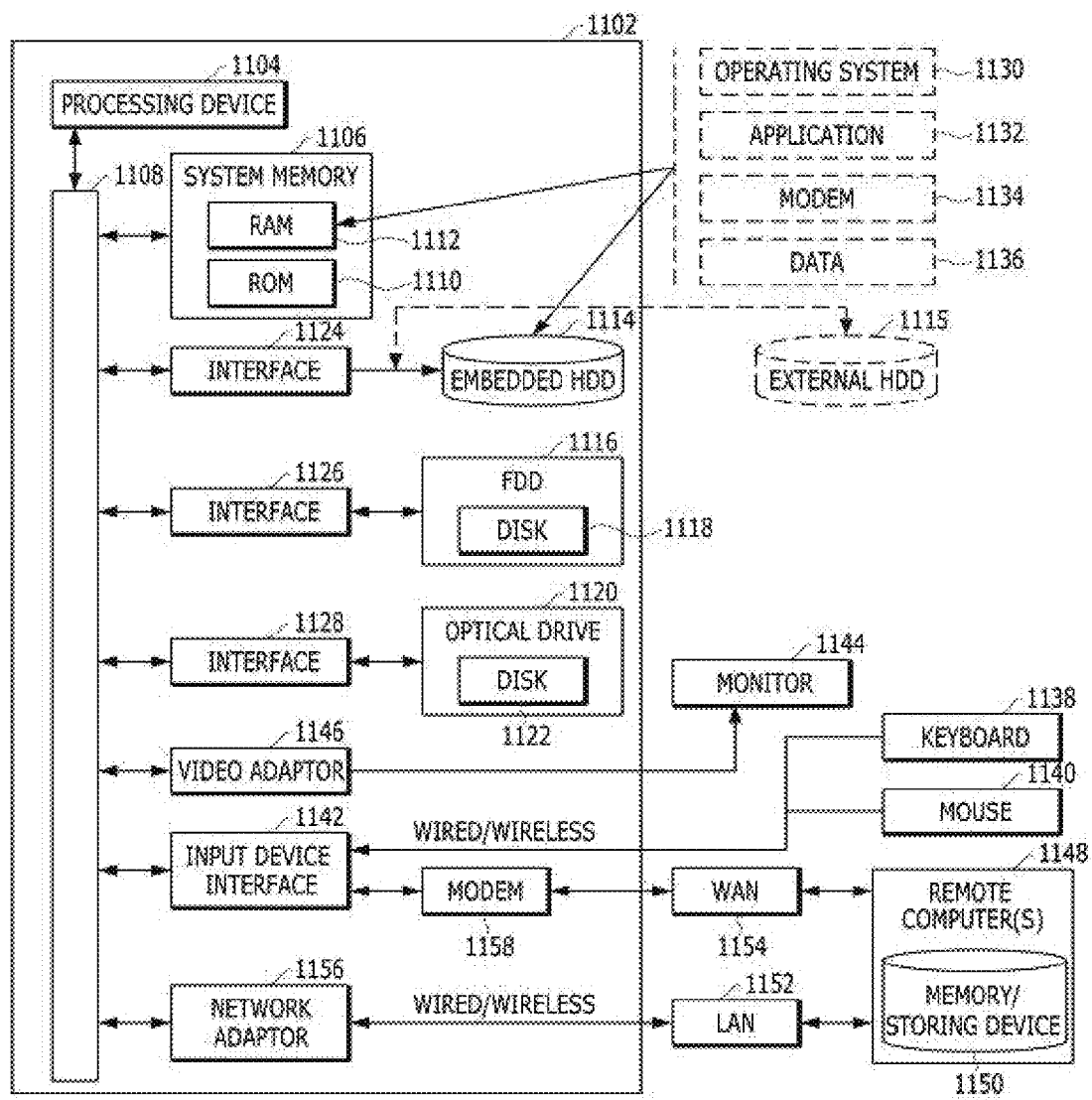
FIG. 12 is a schematic diagram of a computing environment according to an embodiment of the present disclosure.

FIG. 12 is a simple and normal schematic view of a computing environment in which the embodiments of the present disclosure may be implemented.

It is described above that the present disclosure may be generally implemented by the computing device, but those skilled in the art will well know that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The embodiments described in the present disclosure may also be implemented in a distributed computing environment in which predetermined (or selected) tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, temporary and non-temporary media, and movable and non-movable media implemented by a predetermined (or selected) method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined (or selected) other media which may be accessed by the computer or may be used to store desired information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal acquired by configuring or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined (or selected) processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting. The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined (or selected) data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an operating environment and further, the predetermined (or selected) media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor

1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer(s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is and other means configuring a communication link among computers may be used.

The computer 1102 performs an operation of communicating with predetermined (or selected) wireless devices or entities which are disposed and operated by the wireless communication, for example, the printer, a scanner, a desktop and/or a portable computer, a portable data assistant (PDA), a communication satellite, predetermined (or selected) equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11 (a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined (or selected) technologies and techniques. For example, data, instructions, commands, information, signals, bits, symbols, and chips which may be referred in the above description may be expressed by voltages, currents, electromagnetic waves, magnetic fields or particles, optical fields or particles, or predetermined (or selected) combinations thereof.

It may be appreciated by those skilled in the art that various logical blocks, modules, processors, means, circuits, and algorithm steps described in association with the embodiments disclosed herein may be implemented by electronic hardware, various types of programs or design codes (for easy description, herein, designated as software), or a combination of all of them. In order to clearly describe the intercompatibility of the hardware and the software, various components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various embodiments presented herein may be implemented as manufactured articles using a method, an apparatus, or a standard programming and/or engineering technique. The term manufactured article includes a computer program, a carrier, or a medium which is accessible by a predetermined (or selected) computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for predicting disease based on a medical image, performed by a computing device including one or more processors, the method comprising:
   generating a feature vector related to predictive values of brain disease for each of two-dimensional (2D) medical images included in a three-dimensional (3D) medical image, using a pre-trained first model;
   estimating importance indicating prediction accuracy for each of the 2D medical images based on the feature vector, using a pre-trained second model; and
   selecting at least one model input image suitable for prediction of the brain disease from among the 2D medical images based on the importance.

2. The method of claim 1, further comprising:
   extracting a brain parenchyma region from each of the 2D medical images in which a position of a brain region is aligned with respect to a template, using a pre-trained third model.

3. The method of claim 1, wherein the first model generates the feature vector based on the 2D medical images, personal information about a subject of the 3D medical image, and number information indicating positions of the 2D medical images in the 3D medical image.

4. The method of claim 3, wherein the first model includes:
   a first neural network extracting features for prediction of the brain disease from the 2D medical images; and
   a second neural network that outputs the predictive values of brain disease for each of the 2D medical images, based on the features extracted by the first neural network, the personal information, and the number information.

5. The method of claim 1, wherein the importance is estimated based on a tree boosting algorithm used in the second model which takes the feature vector as input.

6. The method of claim 1, wherein the selecting the at least one model input image suitable for prediction of the brain disease includes:
   selecting at least one of the 2D medical images as the model input image by comparing the importance and a threshold value; and
   obtaining reference number information indicating a position of the selected model input image in the 3D medical image.

7. The method of claim 1, further comprising:
   using the selected at least one model input image as training data for a disease diagnosis model.

8. A method for predicting disease based on a medical image, performed by a computing device including one or more processors, the method comprising:
   generating information for parcellating at least one brain region present in each of two-dimensional (2D) medical images included in a three-dimensional (3D) medical image, using a pre-trained segmentation model; and
   selecting an image satisfying predetermined condition related to a reference region from among the 2D medical images based on the generated information for parcellating as at least one model input image suitable for prediction of a brain disease,
   wherein the reference region is a brain region representing a structure for determining the brain disease.

9. The method of claim 8, wherein the reference region includes a medial temporal lobe, and
   wherein the parcellated at least on brain region includes at least one of a hippocampus, a amygdala, a entorhinal cortex, a parahippocampal cortex, or a ventricle.

10. The method of claim 8, further comprising:
    using the selected at least one model input image as training data for a disease diagnosis model.

11. A method for predicting disease based on a medical image, performed by a computing device including one or more processors, the method comprising:
    extracting a brain parenchyma region respectively from two-dimensional (2D) medical images in which a position of a brain region is aligned based on a template, using a pre-trained preprocess model;
    selecting at least one image corresponding to reference number information among the 2D medical images from which the brain parenchyma region is extracted as at least one model input image suitable for prediction of a brain disease; and
    predicting a presence probability of the brain disease based on the selected model input image, using a pre-trained disease diagnosis model.

12. The method of claim 11, wherein the selecting the at least one model input image suitable for prediction of the brain disease includes:
    wherein the reference number information is predetermined based on importance indicating prediction accuracy of the brain disease for each of the 2D medical images included in a three-dimensional (3D) medical image.

13. The method of claim 11, wherein the reference number information is predetermined based on number information indicating where the 2D medical image determined as the model input image is located in a three-dimensional (3D) medical image.

14. The method of claim 11, wherein the disease diagnosis model is trained based on at least one image selected as suitable for prediction of the brain disease among the 2D medical images included in a three-dimensional (3D) medical image.

* * * * *